(12) United States Patent
Gamlin

(10) Patent No.: US 8,906,970 B2
(45) Date of Patent: *Dec. 9, 2014

(54) FISCHER-TROPSCH PROCESS IN A RADIAL REACTOR

(75) Inventor: Timothy Douglas Gamlin, London (GB)

(73) Assignee: Davy Process Technology Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/579,973

(22) PCT Filed: Feb. 6, 2012

(86) PCT No.: PCT/GB2012/050256
§ 371 (c)(1),
(2), (4) Date: Oct. 2, 2012

(87) PCT Pub. No.: WO2012/146903
PCT Pub. Date: Nov. 1, 2012

(65) Prior Publication Data
US 2014/0187653 A1    Jul. 3, 2014

(30) Foreign Application Priority Data
Apr. 27, 2011 (GB) .................................. 1107070.3

(51) Int. Cl.
*C07C 1/04* (2006.01)
*B65D 6/00* (2006.01)
(Continued)

(52) U.S. Cl.
CPC ............... *C07C 1/041* (2013.01); *B01J 8/0214* (2013.01); *B01J 8/0285* (2013.01); *B01J 8/0415* (2013.01); *B01J 8/067* (2013.01); *B01J 19/2485* (2013.01); *C10G 2/341* (2013.01); *B01J 2208/00814* (2013.01); *B01J 2219/00038* (2013.01); *B01J 2219/0004* (2013.01)
USPC ........................... 518/706; 518/700; 518/707

(58) Field of Classification Search
USPC ......................................... 518/700, 707, 706
See application file for complete search history.

(56) References Cited

U.S. PATENT DOCUMENTS 5,545,674 A * 8/1996 Behrmann et al. ............ 518/715
6,323,248 B1   11/2001 Mart et al.

FOREIGN PATENT DOCUMENTS

EP           1300190 A1    4/2003
(Continued)

OTHER PUBLICATIONS

International Search Report and Written Opinion issued in PCT/GB2012/050256, dated May 2, 2012.
(Continued)

*Primary Examiner* — Jafar Parsa
*Assistant Examiner* — Medhanit Bahta
(74) *Attorney, Agent, or Firm* — Armstrong Teasdale LLP

(57) ABSTRACT

In a process for converting synthesis gas to higher hydrocarbons in a tubular reactor, reactants are introduced through an inlet of the reactor. The reactants are passed downwardly through at least one tube to an upper surface of a catalyst carrier where they pass into a passage defined by an inner perforated wall of a catalyst container before passing radially through the catalyst bed towards the perforated outer wall. Reaction occurs as the synthesis gas contacts the catalyst. Unreacted reactant and product is passed out of the container through a perforated outer wall thereof and then upwardly between a skirt and an outer wall of the container, followed by being directed over the end of the skirt and downwardly between the skirt and the reactor tube where heat transfer takes place. These steps are repeated for any subsequent catalyst carrier, then product is removed from an outlet of the reactor.

24 Claims, 5 Drawing Sheets

(51) Int. Cl.
*B01J 8/02* (2006.01)
*B01J 8/06* (2006.01)
*B01J 8/04* (2006.01)
*B01J 19/24* (2006.01)
*C10G 2/00* (2006.01)

(56) References Cited

FOREIGN PATENT DOCUMENTS

| EP | 1623755 | A1 | 2/2006 |
| EP | 1818094 | A1 | 8/2007 |
| WO | 2010069486 | A2 | 6/2010 |
| WO | 2011048361 | A1 | 4/2011 |
| WO | WO 2011048361 | A1 * | 4/2011 |

OTHER PUBLICATIONS

International Preliminary Report on Patentability and Written Opinion for PCT/GB2012/050256 dated Nov. 7, 2013; 7 pages.

* cited by examiner

Detail A

FISCHER-TROPSCH PROCESS IN A RADIAL REACTOR

The present invention relates to a process for the conversion of carbon monoxide and hydrogen (synthesis gas) to liquid hydrocarbon products in the presence of a Fischer-Tropsch catalyst.

In the Fischer-Tropsch synthesis reaction a gaseous mixture of carbon monoxide and hydrogen is reacted in the presence of a catalyst to give a hydrocarbon mixture having a relatively broad molecular weight distribution. The product is predominantly straight chain, saturated hydrocarbons which typically have a chain length of more than 2 carbon atoms, for example, more than 5 carbon atoms.

The ability to build hydrocarbons from synthesis gas is an attractive alternative to production of the hydrocarbons by cracking oil. This approach to hydrocarbon make has increased as oil production has struggled to keep up with increasing demand for high quality fuel and will increase further as oil reserves diminish and those reserves become more carbon rich.

It is therefore desirable to optimise the Fischer-Tropsch process. Several approaches to this have been made and these have generally been directed at reactor design or at the catalyst formulation. One of the major issues with the process is that the heat evolved by the reaction is very substantial being, for example, approximately twice that produced by the reaction to produce methanol for the equivalent conversion of carbon oxides.

One approach to handling the high heat evolved is to carry out the reaction in a fixed bed reactor. In this arrangement, catalyst pellets are loaded inside tubes of an axial reactor. Cooling medium, such as vaporising water, is supplied around the tubes. Reactant gases are then passed through the tubes where they contact the catalyst and the Fischer-Tropsch reaction takes place. The heat evolved is transferred through the tube wall to the surrounding cooling medium. In view of the need to control the heat within the tube, the size of the tubes is limited to allow the heat to pass readily from the centre of the tubes to the walls where heat exchange occurs. Generally therefore the tubes have a diameter of less than about 40 mm to ensure the required level of heat transfer and to prevent the catalyst located towards the centre of the tube overheating and thermal runaway occurring. The small size of the tubes contributes to the high cost of construction of these reactors.

Even at the small tube size the catalyst particles have to be relatively small in order to ensure reasonable mixing and heat transfer. In addition careful selection of conditions such as superficial velocity and gas hourly space velocity has to be made in order to maintain the required heat transfer and manage the conversion of the reactant gases at a reasonable overall pressure drop.

For tubes approaching the upper size limit, it has been proposed to use larger catalyst particle sizes and to incorporate gas and/or liquid recycles to enhance the tube cooling. However, this approach has some disadvantages since there is significant resistance to mass transfer in Fischer-Tropsch catalyst particles where the reactants and lighter products have to travel through wax. This leads to the selectivity to unwanted lighter products increasing and the generation of further unwanted heat at the centre of the particle.

In an attempt to address these problems so-called "eggshell" catalysts have been proposed in which the surface of a support is impregnated. However, these catalysts provide less active catalyst per unit volume of the reactor and therefore reduce the productivity, and hence economics, of the process.

It has also been proposed to reduce the carbon monoxide to hydrogen ratio in the reactant gas to improve the mass transfer of the carbon monoxide to the centre of the catalyst particle. Whilst this does improve the catalyst selectivity, the reaction kinetics are slowed which can lead to various problems such as carbide formation which has to be removed periodically.

A further problem is that reduced catalyst cannot generally be used in fixed bed reactors so equipment has to be in place to cater for initial reduction to allow for regeneration of the catalyst if required. In some cases this requires the reactor vessel design conditions to be considerably in excess of the normal operating conditions thereby increasing capital costs.

An alternative approach is to carry out the reaction in a bubble slurry reactor. In this arrangement, small catalyst particles, such as those of 150 μm or less, are suspended in the hydrocarbon product and are agitated by the injection of reaction gas at the bottom of the reactor. The gas becomes highly dispersed throughout the reactor and so, in theory, the mass transfer area from gas to catalyst is very large. Additionally, as the catalyst diameter is low, the mass transfer and heat transfer resistances within the catalyst particle are also low. Since the catalyst surface area is relatively large the heat transfer from catalyst particle to fluid is high so that the particles can be maintained at approaching fluid temperature conditions. The high heat evolution in the reaction can be managed with internal or external coils in which water is vaporised. Thus in theory, carrying out the process in a bubble slurry reactor offers various advantages.

However, in practice there can be significant mass transfer resistances in the bubble slurry reactors such that high water partial pressures can be experienced inside the catalyst particles. Workers have reported issues such as catalyst oxidation and catalyst damage due to hydrothermal attack of the catalyst support structures. In addition, catalyst attrition can be a significant problem which can lead to product purity and catalyst loss issues caused by the difficulty of arranging adequate separation of very small particles from the product.

Further cobalt based Fischer-Tropsch catalysts can be susceptible to poisoning by even very low levels of impurities such as sulphur species. This is a particular issue in bubble slurry reactors since, if the synthesis gas includes poisons, all the catalyst within the reactor will be exposed to the poison whereas in fixed bed reactors the first catalyst to be exposed to the poison tends to act as a guard bed for subsequent catalyst.

It will therefore be understood that bubble slurry reactors provide a challenging environment for catalysts and therefore long catalyst charge lives are difficult to achieve leading to frequent or continuous removal of spent catalyst and replacement with fresh catalyst charge which results in reduced average production per unit of catalyst and increases the cost of operating the system.

Further, in order to optimise the operation of the bubble slurry reactor, it has to be relatively tall in order to achieve the required level of agitation and mass transfer. Sufficient liquid has to be contained in the reactor to accommodate the catalyst at concentrations in the region of 20 to 30 weight percent which results in a large volume of contained liquid. When these reactors are operating, the gas hold ups within the slurry are also significant. This requires extra reactor capacity to accommodate the slurry bed in the gassed state. To accommodate this, the reactors are generally of the order of 60 m in height. Such large reactors are heavy which makes them expensive and difficult to deploy. If the plant site is not proximate to a substantial waterway, the transport issues of such a large reactor become critical.

More recently, it has been suggested that a so-called microchannel reactor can be used to improve the Fischer-Tropsch reaction system by process intensification. Key to this approach is to carry out the reaction in narrow channels between the plates of a steam raising reactor. In this arrangement high heat transfer coefficients and high specific productivities can be achieved. This approach also enables mass transfer resistances to be minimised by using highly active catalysts on extended surfaces.

These micro-channel reactors are made by bonding plates to form passages for the flow of the cooling medium. These reactors have to be fabricated by specialists and have to be contained in containment vessels. Thus the capital costs of these arrangements are substantial. A further problem is that there is a limit to the size at which modular units can be manufactured and the reactors surprisingly have a high specific weight per unit of production making them costly to manufacture.

As high specific activity is required of the catalysts used in micro-channel reactors, they tend to operate at higher temperatures and produce products at the lighter end of the hydrocarbon chain spectrum.

A further problem associated with micro-channel reactors relates to the risk of poisoning, to which as indicated above, Fischer-Tropsch catalysts are particularly susceptible. In a micro-channel reactor the relative amount of catalyst used is low and therefore if poisoning occurs, a significant reduction in performance will also be observed. If the catalyst becomes deactivated, the developers have stated that it is necessary to return the reactor module to the factory to have the catalyst removed and replaced, resulting in high cost and significant downtime unless costly reactors are maintained as spares. Thus micro-channel reactors are generally only used in small capacity situations such as in so-called "flare busting" duties where performance and costs are less than the problems associated with the disposal of inconvenient gas.

An alternative arrangement is discussed in WO 2010/069486 in which a number of adiabatic reactors are arranged in series. Since the temperature rises described are substantial, this arrangement would not be expected to deliver good performance with conventional Fischer-Tropsch catalysts. In particular, the high temperatures would be expected to cause rapid catalyst deactivation. In addition at a reasonable overall conversion, a high methane make would be expected.

Thus it will be understood that whilst the various approaches to carrying out Fischer-Tropsch reactions each offer some advantages, they also each have their own disadvantages. There is therefore still a need to provide an improved Fischer-Tropsch process which addresses one or more of the problems of prior art arrangements.

According to the present invention there is provided a process for the conversion of synthesis gas to higher hydrocarbons by contacting a gaseous stream comprising synthesis gas with a particulate Fischer-Tropsch catalyst, said process being carried out in a tubular reactor having an inlet and an outlet, said outlet being located downstream of the inlet, said reactor comprising one or more tubes having located therein one or more carriers for said particulate catalyst and cooling medium in contact with said at least one tube;
wherein said catalyst carrier comprises:
an annular container holding catalyst, said container having a perforated inner wall defining a tube, a perforated outer wall, a top surface closing the annular container and a bottom surface closing the annular container;
a surface closing the bottom of said tube formed by the inner wall of the annular container;
a skirt extending upwardly from the perforated outer wall of the annular container from a position at or near the bottom surface of said container to a position below the location of a seal; and
a seal located at or near the top surface and extending from the container by a distance which extends beyond an outer surface of the skirt; said process comprising:
(a) introducing the gaseous reactants through the inlet;
(b) passing said reactants downwardly through said at least one tube to the upper surface of the, or the first, catalyst carrier where they pass into the passage defined by the inner perforated wall of the container before passing radially through the catalyst bed towards the perforated outer wall;
(c) allowing reaction to occur as the synthesis gas contacts the catalyst;
(d) passing unreacted reactant and product out of the container though the perforated outer wall and then upwardly between the inner surface of the skirt and the outer wall of the annular container until they reach the seal where they are directed over the end of the skirt and caused to flow downwardly between the outer surface of the skirt and the inner surface of the reactor tube where heat transfer takes place;
(e) repeating steps (b) to (d) at any subsequent catalyst carrier; and
(f) removing product from the outlet.

The catalyst carrier is described in detail in PCT/GB2010/001931 filed on 19 Oct. 2010 which is incorporated herein by reference.

For the avoidance of doubt, any discussion of orientation, for example terms such as upwardly, below, lower, and the like have, for ease of reference been discussed with regard to the orientation of the catalyst carrier as illustrated in the accompanying drawings. However, where the tubes, and hence the catalyst carrier, are used in an alternative orientation, the terms should be construed accordingly.

The catalyst container will generally be sized such that it is of a smaller dimension than the internal dimension of the reactor tube into which it is placed. The seal is sized such that it interacts with the inner wall of the reactor tube when the catalyst carrier of the present invention is in position within the tube. The seal need not be perfect provided that it is sufficiently effective to cause the majority of the flowing gas to pass through the carrier.

Generally, a plurality of catalyst carriers will be stacked within the reactor tube. In this arrangement, the reactants/products flow downwardly between the outer surface of the skirt of a first carrier and the inner surface of the reactor tube until they contact the upper surface and seal of a second carrier and are directed downwardly into the tube of the second carrier defined by the perforated inner wall of its annular container. The flow path described above is then repeated.

The catalyst carrier may be formed of any suitable material. Such material will generally be selected to withstand the Operating conditions of the reactor. Generally, the catalyst carrier will be fabricated from carbon steel, aluminium, stainless steel, other alloys or any material able to withstand the reaction conditions.

The wall of the annular container can be of any suitable thickness. Suitable thickness will be of the order of about 0.1 mm to about 1.0 mm, preferably of the order of about 0.3 mm to about 0.5 mm.

The size of the perforations in the inner and outer walls of the annular container will be selected such as to allow uniform flow of reactant(s) and product(s) through the catalyst while maintaining the catalyst within the container. It will therefore be understood that their size will depend on the size of the catalyst particles being used. In an alternative arrangement the perforations may be sized such that they are larger but have a filter mesh covering the perforations to ensure catalyst is maintained within the annular container. This enables larger perforations to be used which will facilitate the free movement of reactants without a significant loss of pressure.

It will be understood that the perforations may be of any suitable configuration. Indeed where a wall is described as perforated all that is required is that there is means to allow the reactants and products to pass through the walls. These may be small apertures of any configuration, they may be slots, they may be formed by a wire screen or by any other means of creating a porous or permeable surface.

Although the top surface closing the annular container will generally be located at the upper edge of the or each wall of the annular container, it may be desirable to locate the top surface below the upper edge such that a portion of the upper edge of the outer wall forms a lip. Similarly, the bottom surface may be located at the lower edge of the, or each, wall of the annular container or may be desirable to locate the bottom surface such that it is above the bottom edge of the wall of the annular container such that the wall forms a lip.

The bottom surface of the annulus and the surface closing the bottom of the tube may be formed as a single unit or they may be two separate pieces connected together. The two surfaces may be coplanar but in a preferred arrangement, they are in different planes. In one arrangement, the surface closing the bottom of the tube is in a lower plane than the bottom surface of the annular container. This serves to assist in the location of one carrier on to a carrier arranged below it when a plurality of containers are to be used. It will be understood that in an alternative arrangement, the surface closing the bottom of the tube may be in a higher plane that the bottom surface of the annular container.

Whilst the bottom surface will generally be solid, it may include one or more drain holes. Where one or more drain holes are present, they may be covered by a filter mesh. Similarly a drain hole, optionally covered with a filter mesh may be present in the surface closing the bottom of the tube. Where the carrier is to be used in a non-vertical orientation, the drain hole, where present will be located in an alternative position i.e. one that is the lowest point in the carrier when in use.

One or more spacer means may extend downwardly from the bottom surface of the annular container. The, or each, spacer means may be formed as separate components or they may be formed by depressions in the bottom surface. Where these spacer means are present they assist in providing a clear path for the reactants and products flowing between the bottom surface of the first carrier and the top surface of a second lower carrier in use. The spacer may be of the order of about 4 mm to about 15 mm, or about 6 mm, deep. Alternatively, or additionally, spacer means may be present on the top surface.

The top surface closing the annular container may include on its upper surface means to locate the container against a catalyst carrier stacked above the container in use. The means to locate the container may be of any suitable arrangement. In one arrangement it comprises an upstanding collar having apertures or spaces therein to allow for the ingress of reactants.

The upwardly extending skirt may be smooth or it may be shaped. Any suitable shape may be used. Suitable shapes include pleats, corrugations, and the like. The pleats, corrugations and the like will generally be arranged longitudinally along the length of the carrier. The shaping of the upstanding skirt increases the surface area of the skirt and assists with the insertion of the catalyst carrier into the reaction tube since it will allow any surface roughness on the inner surface of the reactor tube or differences in tolerances in tubes to be accommodated.

Where the upwardly extending skirt is shaped, it will generally be flattened to a smooth configuration towards the point at which it is connected to the annular container to allow a gas seal to be formed with the annular container. The upstanding skirt will generally be connected to the outer wall of the annular container at or near the base thereof. Where the skirt is connected at a point above the bottom of the wall, the wall will be free of perforations in the area below the point of connection. The upstanding skirt may be flexible.

Generally, the upstanding skirt will stop at about 0.5 cm to about 1.5 cm, preferably about 1 cm, short of the top surface of the annular container.

Without wishing to be bound by any theory, it is believed that the upstanding skirt serves to gather the reactants/products from the perforated outer wall of the annular container and direct them via the shapes towards the top of the catalyst carrier collecting more reactants/products exiting from the outer wall of the annular container as they move upwardly. As described above, reactants/products are then directed down between the tube wall and the outside of the upstanding skirt. By this method the heat transfer is enhanced down the whole length of the carrier but as the heat exchange is separated from the catalyst, hotter or colder as appropriate heat exchange fluid can be used without quenching the reaction at the tube wall and at the same time ensuring that the temperature of the catalyst towards the centre of the carrier is appropriately maintained.

The seal may be formed in any suitable manner. However, it will generally be sufficiently compressible to accommodate the smallest diameter of the reactor tube. The seal will generally be a flexible, sliding seal. In one arrangement, an O-ring may be used. A compressible split ring or a ring having a high coefficient of expansion could be used. The seal may be formed of any suitable material provided that it can withstand the reaction conditions. In one arrangement, it may be a deformable flange extending from the carrier. The flange may be sized to be larger than the internal diameter of the tube such that as the container is inserted into the tube it is deformed to fit inside and interact with the tube.

In the present invention, the annular space between the outer surface of the catalyst container and the inner surface of the tube wall is small, generally of the order of from about 3 mm to about 10 mm. This narrow gap allows a heat transfer coefficient to be achieved such that an acceptable temperature difference of the order of about 10° C. to about 40° C. between the cooled exit gas and the coolant to be achieved.

The size of the annulus between the skirt and the catalyst wall and the skirt and the tube wall will generally be selected to accommodate the gas flow rate required while maintaining high heat transfer and low pressure drop. Thus the process of the present invention may additional include the step of selecting the appropriate size of the annulus to meet these criteria.

The process of the present invention enables relatively large reactor tubes to be used. In particular, tubes having diameters in the region of from about 75 mm to about 130 mm or even about 150 mm can be used compared to diameters of less than about 40 mm used in conventional systems. The larger diameter tubes will allow capacity in the region of 10,000 US bbl/day to be achieved in a single reactor of less than 6 m in diameter and less than 700 tonnes in weight.

As discussed above the highly exothermic nature of the Fischer-Tropsch reaction is a major factor in the design of a reactor in which the reaction can be carried out. The use of the catalyst carrier in the process of the present invention, allows tubes comprising a plurality of catalyst carriers to become, in effect, a plurality of adiabatic reactors with inter-cooling.

Any suitable catalyst may be used in the process of the present invention. Powdered, foamed, structured, or other suitable forms may be used.

One benefit of the process of the present invention is that the carrier allows for the deployment of small diameter Fischer-Tropsch catalysts to be used such as those having diameters of from about 100 μm to about 1 mm. Since these are used in a fixed bed, the mass transfer resistances can be greatly reduced over prior art arrangements. This will lead to improved selectivity to the required products, particularly those having a carbon chain length of five and above.

Further, as these small catalysts have a high surface area and are located in the direct flow of the reacting gas, they are maintained at a temperature which is very similar to that of the flowing gas. This will reduce the tendency to by-product formation.

In one alternative arrangement, a monolith catalyst may be used. In this arrangement, the structure of the catalyst container may be modified. Full details of a catalyst container suitable for use with a monolith catalyst is described in GB patent application no 1105691.8 filed 4 Apr. 2011 the contents of which are incorporated herein by reference.

Thus according to a second aspect of the present invention there is provided a process for the conversion of synthesis gas to higher hydrocarbons by contacting a gaseous stream comprising synthesis gas with a monolith Fischer-Tropsch catalyst, said process being carried out in a tubular reactor having an inlet and an outlet, said outlet being located downstream of the inlet, said reactor comprising one or more tubes having located therein one or more carriers for said monolith catalyst and cooling medium in contact with said tubes; wherein said catalyst carrier comprises:

- a container holding a monolith catalyst, said container having a bottom surface closing the container and a skirt extending upwardly from the bottom surface of said container to a position below the location of a seal and spaced therefrom, said skirt being positioned such that there a space between an outer surface of the monolith catalyst and the skirt; and
- a seal located at or near a top surface of the monolith catalyst and extending from the monolith catalyst by a distance which extends beyond an outer surface of the skirt; said process comprising:
  (a) introducing the gaseous reactants through the inlet;
  (b) passing said reactants downwardly through said at least one tube to the upper surface of the, or the first, monolith catalyst where they pass through the monolith catalyst;
  (c) allowing reaction to occur as the synthesis gas contacts the catalyst;
  (d) passing unreacted reactant and product out of the catalyst and then upwardly between the inner surface of the skirt and the outer surface of the monolith catalyst until they reach the seal where they are directed over the end of the skirt and caused to flow downwardly between the outer surface of the skirt and the inner surface of the reactor tube where heat transfer takes place;
  (e) repeating steps (b) to (d) at any subsequent catalyst carrier; and
  (f) removing product from the outlet.

In one arrangement, the monolith catalyst is a solid, in that there is substantially no space within the body of the monolith that is not occupied by catalyst. When the monolith is in use in a vertical reactor with downflow, the reactant(s) flow downwardly through the reactor tube, the reactant(s) first contacts the upper face of the monolith catalyst and flows therethrough in a direction parallel to the axis of the cylinder. The seal of the container prevents the reactant(s) from flowing around the monolith and assists the direction of the reactants into the catalyst. Reaction will then occur within the monolith catalyst. The product will then also flow down through the monolith in a direction parallel to the axis of the cylinder.

Once the reactant(s) and product reach the bottom surface of the catalyst carrier they are directed towards the skirt of the carrier. To facilitate this flow, feet may be provided within the carrier on the upper face of the bottom surface such that, in use, the catalyst monolith is supported on the feet and there is a gap between the bottom of the catalyst monolith and the bottom surface of the catalyst carrier. The upwardly extending skirt then directs the reactant(s) and product upwardly between the inner surface of the skirt and the outer surface of the monolith catalyst until they reach the underside of the seal. They are then directed, by the underside of the seal, over the end of the skirt and they then flow downwardly between the outer surface of the skirt and the inner surface of the reactor tube where heat transfer takes place.

In one alternative arrangement, the monolith catalyst has a channel extending longitudinally therethrough. Generally the channel will be located on the central axis of the monolith catalyst. Thus where the reactor tube is of circular cross-section, the monolith catalyst of this arrangement will be of annular cross-section. In this arrangement, in use, in a vertical reactor with downflow, reactant(s) flow downwardly through the reactor tube and thus first contacts the upper surface of the monolith catalyst. The seal blocks the passage of the reactant(s) around the side of the catalyst. Since the path of flow of reactant(s) is impeded by the catalyst, it will generally take the easier path and enter the channel in the monolith. The reactant(s) then enters the annular monolith catalyst and passes radially through the catalyst towards the outer surface of the catalyst monolith. During the passage through the catalyst monolith reaction occurs. Unreacted reactant and product then flow out of the monolith catalyst though the outer surface thereof. The upwardly extending skirt then directs reactant and product upwardly between the inner surface of the skirt and the outer wall of the monolith catalyst until they reach the seal. They are then directed, by the underside of the seal, over the end of the skirt and flow downwardly between the outer surface of the skirt and the inner surface of the reactor tube where heat transfer takes place.

In the arrangement in which the monolith catalyst includes the channel, the catalyst carrier may include a top surface which will extend over the monolith catalyst but leave the channel uncovered. This top surface serves to ensure that the reactant(s) do not enter the catalyst monolith from the top but are directed into the channel for radial flow.

The discussion of the specific features of the catalyst carrier above in relation to the first embodiment applies equally in connection to the catalyst carrier for a monolith catalyst of the second embodiment insofar as the relevant features are present.

Whichever type of carrier is used, in one arrangement more than 40 carriers, preferably more than 41 carriers are located within a single tube. More preferably, from about 70 to about 200 carriers may be used. This will enable a reasonable temperature rise of the order of from about 10° C. to about 20° C. to be maintained over each stage.

The radial flow through the, or each, catalyst carrier within the tube means that the gas flow path length is also very low when compared with prior art arrangements. Total catalyst depths of the order of about 2 meters may be achieved within a tube of up to 20 meters of length at catalyst hourly space velocities of about 4000. The low flow path means that the overall pressure drop achieved is an order of magnitude lower than that which would be experienced with the same catalyst in an axial tube not using the process of the present invention.

One advantage of being able to achieve a low overall pressure drop by the process of the present invention is that long tubes with high superficial gas velocities, gases containing high quantities of inerts or a gas recycle may be accommodated without the pressure drop and potential for catalyst crushing disadvantages experienced with high flows through current fixed bed systems. The ability to accommodate recycle will enable overall conversion at lower per pass conversions to be achieved at high catalyst productivity and selectivity.

The reduced catalyst may be repeatedly and reliably reduced and loaded into the carrier at a manufacturing facility and the balance of the container can be filled with wax. The containers may be assembled in connected units which will simplify the loading of the reactor and in particular will mean that the operators do not have to come into contact with the catalyst. The unloading procedure is also simplified since the carriers may be readily discharged before being taken for reprocessing.

In one arrangement of the present invention, a plurality of reactors may be used in parallel.

Liquid product stream separated from the stream exiting the reactor will be recovered. In the process of the present invention, unreacted gas exiting the outlet of the, or each, reactor may be further treated to remove heat. The removed heat may be reused and/or rejected to cooling. Liquid product separated from the stream exiting the reactor will be recovered.

In one arrangement, two or more reactors may be located in series fluid communication with facilities located between each reactor to remove heat. The heat may be reused and/or rejected to cooling. In one arrangement, hydrogen and carbon monoxide containing steam exiting the last stage of a series of interconnected reactors may be recycled to any suitable point in the process. In one arrangement it will be recycled to the inlet of the first reactor.

In one alternative arrangement, two or more groups of parallel reactors may be located in series. In this arrangement, groups of parallel reactors are in series communication with facilities located between each group to remove heat. The heat may be reused and/or rejected to cooling. In one arrangement, liquid product may be removed between each stage with hydrogen and carbon monoxide containing steam being passed to a subsequent reactor group in the series. Hydrogen and carbon monoxide containing steam exiting the last stage of a series of interconnected reactors may be recycled to any suitable point in the process. In one arrangement it will be recycled to the inlet of the first reactor.

Where the process includes a plurality of reaction stages, a hydrogen rich stream may be fed to the second and/or one or more of any subsequent stages.

Any suitable reaction conditions may be used. In one arrangement, the reaction temperature will be from about 190° C. to about 250° C. The reaction pressure may be from about 20 bara to about 80 bara.

The present invention will now be described, by way of example, by reference to the accompanying drawings in which.

Figure 1:
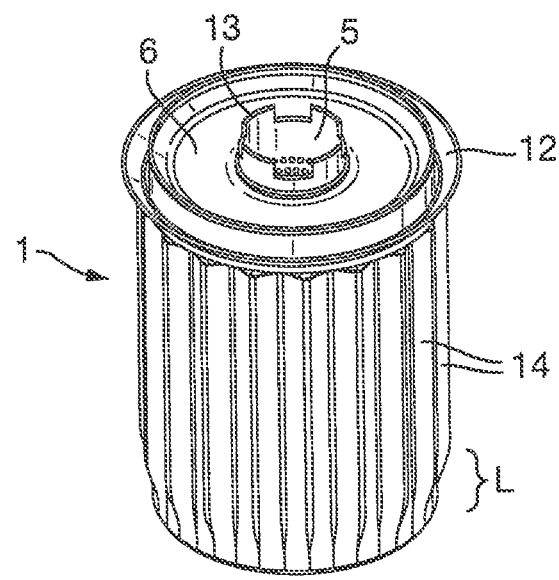
FIG. 1 is a perspective view from above of the catalyst carrier of the present invention.
Figure 2:
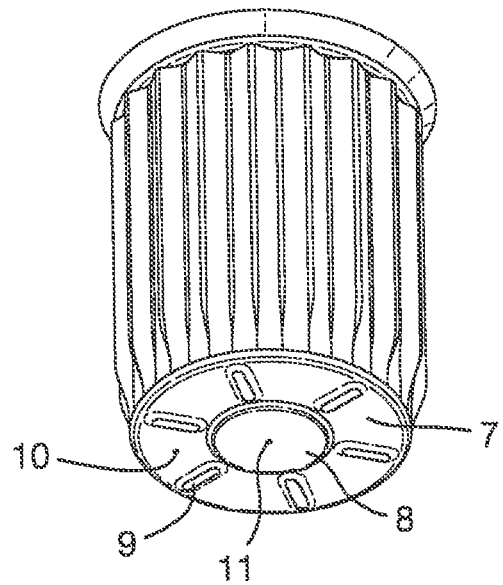
FIG. 2 is a perspective view of the catalyst carrier from below.
Figure 3:
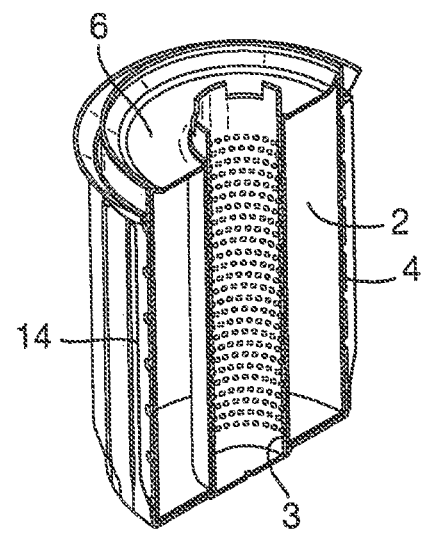
FIG. 3 is a partial cross section viewed from the side.

A catalyst carrier 1 of the present invention is illustrated in FIGS. 1 to 3. The carrier comprises an annular container 2 which has perforated walls 3, 4. The inner perforated wall 3 defines a tube 5. A top surface 6 is closes the annular container at the top. It is located at a point towards the top of the walls 3, 4 of the annular container 2 such that a lip 6 is formed. A bottom surface 7 closes the bottom of the annular container 2 and a surface 8 closes the bottom of tube 5. The surface 8 is located in a lower plane that that of the bottom surface 7. Spacer means in the form of a plurality of depressions 9 are located present on the bottom surface 7 of the annular container 2. Drain holes 10, 11 are located on the bottom surface 7 and the surface 8.

A seal 12 extends from the upper surface 6 and an upstanding collar 13 is provided coaxial with the tube 5.

A corrugated upstanding skirt 14 surrounds the container 2. The corrugations are flattened in the region L towards the base of the carrier 1.

Figure 4:
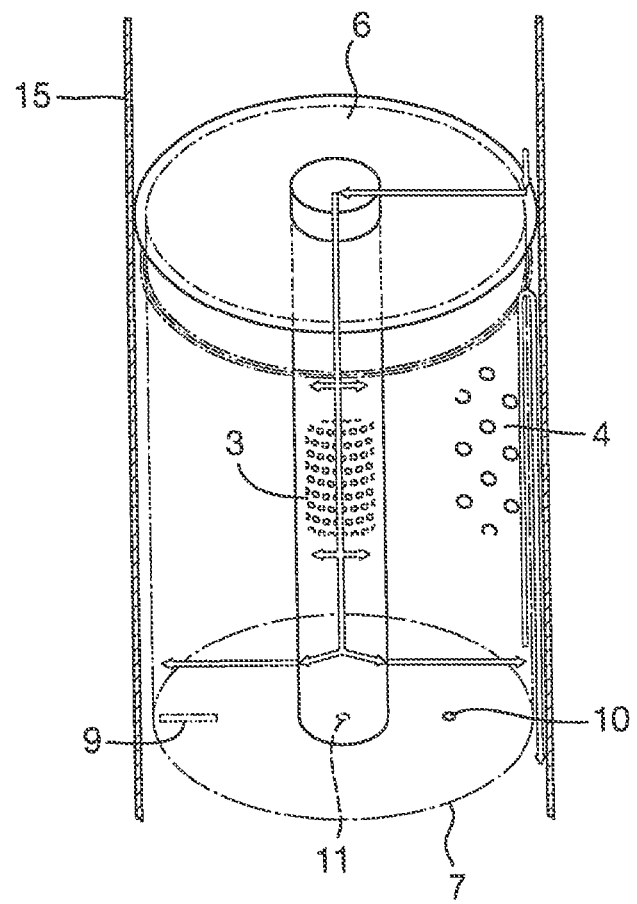
FIG. 4 is a simplified diagram of the catalyst carrier of the present invention.
Figure 5:
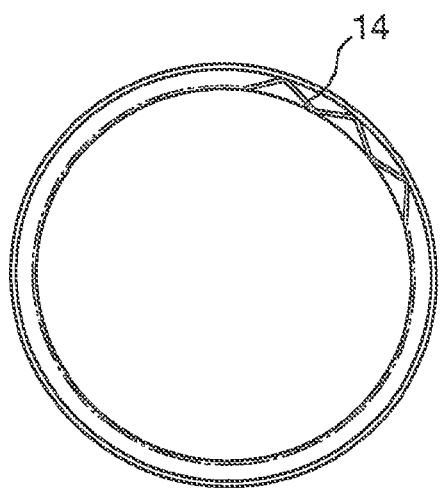
FIG. 5 is a schematic illustration of a carrier of the present invention from below when located within a tube.

A catalyst carrier 1 of the present invention located in a reactor tube 15. The flow of gas is illustrated schematically in FIG. 4 by the arrows.

Figure 6:
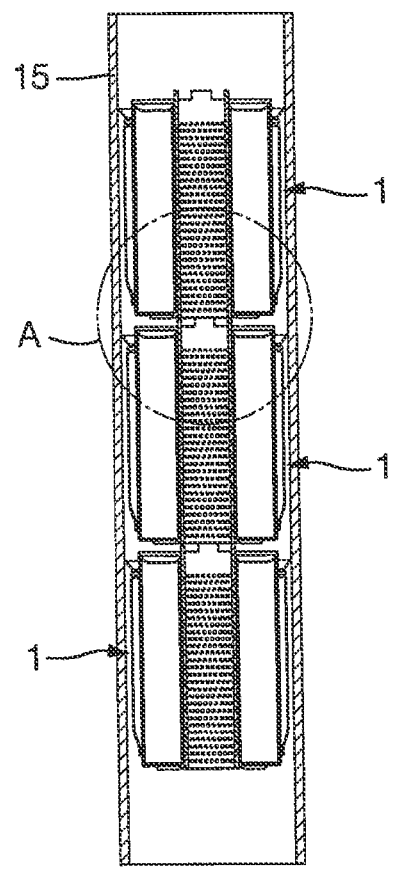
FIG. 6 is a schematic cross section of three catalyst carriers located within a tube.
Figure 7:
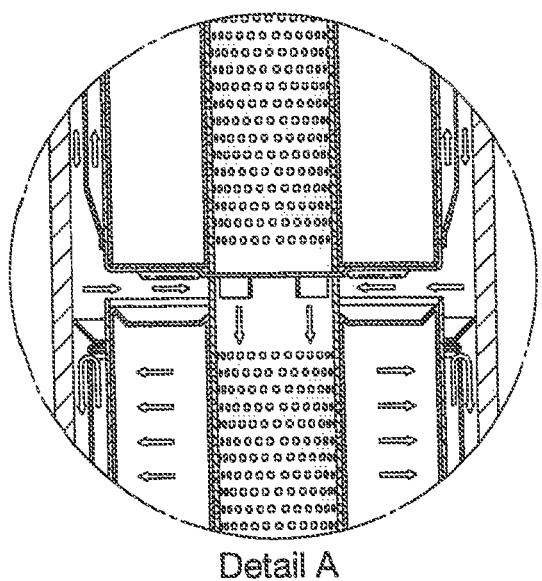
FIG. 7 is an enlarged cross-section of Section A of FIG. 6.

When a plurality of catalyst carriers of the present invention are located within a reactor tube 15 they interlock as illustrated in FIGS. 6 and 7. The effect on the flow path is illustrated in the enlarged section shown in FIG. 7.

Figure 8:
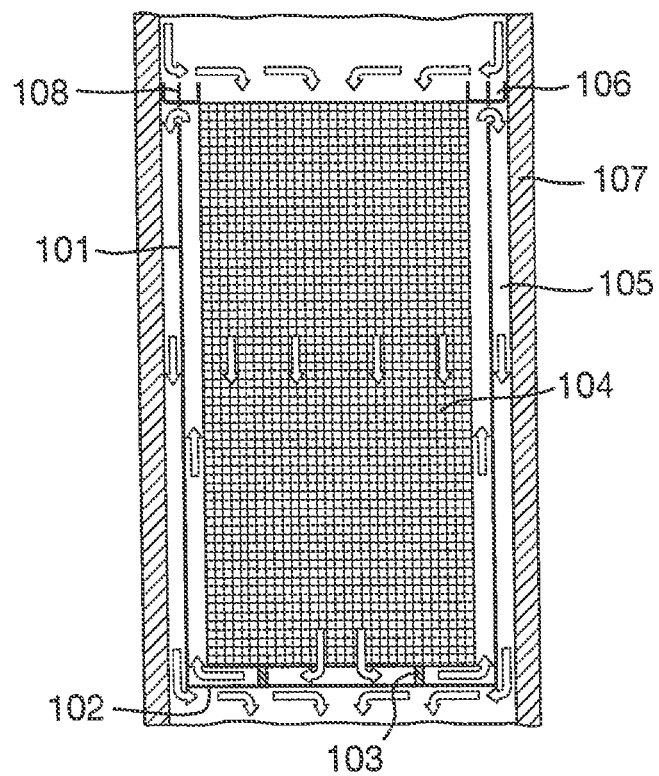
FIG. 8 is a schematic representation of an alternative embodiment of the present invention, illustrating the flow path.

A catalyst carrier 101 of a second embodiment is illustrated in FIG. 8. A bottom surface 102 closes the bottom of the container 101. Feet 103 extend upwardly from the bottom surface to support a monolith catalyst 104. An upstanding skirt 105 extends from the bottom surface 102. The skirt may be corrugated and may be flattened as in a region towards the bottom surface 103.

A seal 106 is provided to extend from the monolith catalyst 104 and interact with the wall of the reactor tube 107. Baffles 108 extend upwardly for the seal. These serve to direct flow and to separate the carrier from the bottom surface of a carrier located above the carrier. The flow of gas is illustrated schematically by the arrows.

Figure 9:
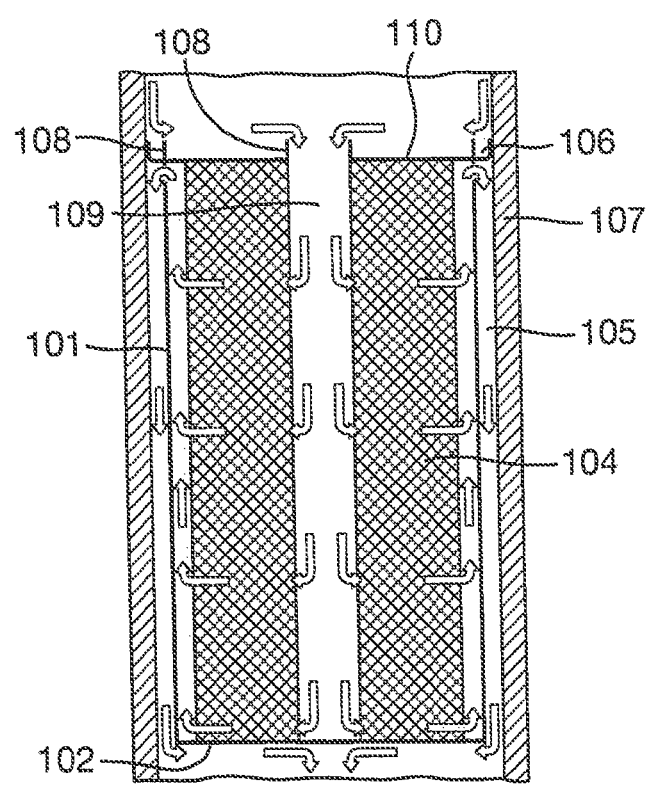
FIG. 9 is a schematic representation of a third embodiment of the present invention, illustrating the flow path.

An alternative embodiment of the present invention is illustrated in FIG. 9. In this arrangement the monolith catalyst 104 has a longitudinal channel 109 therethrough. In this arrangement, the feet of the first embodiment may be omitted. This carrier is similar in arrangement to the first embodiment. However, additionally a top surface 110 is provided to cover the upper surface of the monolith catalyst. The flow of gas in the arrangement of FIG. 9 is illustrated schematically by the arrows.

Figure 10:
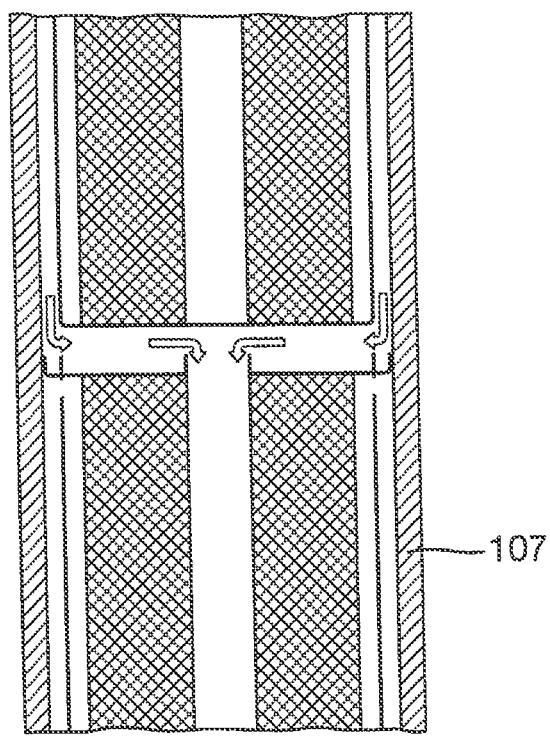
FIG. 10 is a schematic representation of the flow path between two stacked carriers of the kind illustrated in FIG. 9.

When a plurality of catalyst carriers of the present invention are located within a reactor tube 107 the effect on the flow path is illustrated in the enlarged section shown in FIG. 10.

It will be understood that whilst the catalyst carriers have been described with particular reference to a use in a tube of circular cross-section the tube may be of non-circular cross-section for example, it may be a plate reactor. Where the tube is of non-circular cross-section, the carrier will be of the appropriate shape. In this arrangement, in the the embodiment described in which an annular monolith is used it will be understood that the monolith will not be a circular ring and this term should be construed accordingly.

The present invention will now be discussed with reference to the following example.

EXAMPLE 1

Conventional fixed bed reactors, currently in production are capable of producing approximately 5833 US barrels/day of Fischer-Tropsch liquids. Public disclosures indicate that these reactors weight 1200 tonnes and have a diameter of 7.2 m and contain over 28000 tubes. A reactor for the process of the present invention processing feed gas containing hydrogen and carbon monoxide derived from natural gas with a diameter of 5.6 m will produce around 10000 US barrels/day of Fischer-Tropsch liquids and will contain approximately 2300 axial tubes each filled with about 80 catalyst carriers and will weigh approximately 700 tonnes. It will therefore be understood that this represents an improvement of almost a factor of three in the specific weight installed per unit of production over the prior art arrangements.

The invention claimed is:

1. A process for the conversion of synthesis gas to higher hydrocarbons by contacting a gaseous stream comprising synthesis gas with a particulate Fischer Tropsch catalyst, said process being carried out in a tubular reactor having an inlet and an outlet, said outlet being located downstream of the inlet, said reactor comprising one or more tubes having located therein one or more carriers for said particulate catalyst and cooling medium in contact with said tubes;
wherein said catalyst carrier comprises:
  an annular container for holding catalyst in use, said container having a perforated inner wall defining a tube, a perforated outer wall, a top surface closing the annular container and a bottom surface closing the annular container;
  a surface closing the bottom of said tube formed by the inner wall of the annular container;
  a skirt extending upwardly from the perforated outer wall of the annular container from a position at or near the bottom surface of said container to a position below the location of a seal; and
  a seal located at or near the top surface and extending from the container by a distance which extends beyond an outer surface of the skirt; said process comprising:
  (a) introducing the gaseous reactants through the inlet;
  (b) passing said reactants downwardly through said at least one tube to the upper surface of the, or the first, catalyst carrier where they pass into the passage defined by the inner perforated wall of the container before passing radially through the catalyst bed towards the perforated outer wall;
  (c) allowing reaction to occur as the synthesis gas contacts the catalyst;
  (d) passing unreacted reactant and product out of the container though the perforated outer wall and then upwardly between the inner surface of the skirt and the outer wall of the annular container until they reach the seal where they are directed over the end of the skirt and caused to flow downwardly between the outer surface of the skirt and the inner surface of the reactor tube where heat transfer takes place;
  (e) repeating steps (b) to (d) at any subsequent catalyst carrier; and
  (f) removing product from the outlet.

2. The process according to claim 1 wherein the catalyst particles have a diameter of from about 100 μm to about 1 mm.

3. A process for the conversion of synthesis gas to higher hydrocarbons by contacting a gaseous stream comprising synthesis gas with a monolith Fischer Tropsch catalyst, said process being carried out in a tubular reactor having an inlet and an outlet, said outlet being located downstream of the inlet, said reactor comprising one or more tubes having located therein one or more carriers for said monolith catalyst and cooling medium in contact with said tubes;
wherein said catalyst carrier comprises:
  a container holding a monolith catalyst, said container having a bottom surface closing the container and a skirt extending upwardly from the bottom surface of said container to a position below the location of a seal and spaced therefrom, said skirt being positioned such that there is a space between an outer surface of the monolith catalyst and the skirt; and
  a seal located at or near a top surface of the monolith catalyst and extending from the monolith catalyst by a distance which extends beyond an outer surface of the skirt; said process comprising:
  (a) introducing the gaseous reactants through the inlet;
  (b) passing said reactants downwardly through said at least one tube to the upper surface of the, or the first, monolith catalyst where they pass through the monolith catalyst;
  (c) allowing reaction to occur as the synthesis gas contacts the catalyst;
  (d) passing unreacted reactant and product out of the catalyst and then upwardly between the inner surface of the skirt and the outer surface of the monolith catalyst until they reach the seal where they are directed over the end of the skirt and caused to flow downwardly between the outer surface of the skirt and the inner surface of the reactor tube where heat transfer takes place;
  (e) repeating steps (b) to (d) at any subsequent catalyst carrier; and
  (f) removing product from the outlet.

4. The process according to claim 1 wherein a plurality of catalyst carriers are stacked within the reactor tube.

5. The process according to claim 1 wherein the annular space between the outer surface of the catalyst container and the inner surface of the tube wall is selected to accommodate the gas flow rate required while maintaining high heat transfer and low pressure drop.

6. The process according to claim 1 wherein the annular space between the outer surface of the catalyst container and the inner surface of the tube wall is of the order of from about 3 mm to about 10 mm.

7. The process according to claim 1 wherein the one or more tubes have a diameter of from about 75 mm to about 150 mm.

8. The process according to claim 1 wherein more than 41 carriers are located within a single tube.

9. The process according to claim 1 wherein from about 70 to about 200 carriers are located within a single tube.

10. The process according to claim 1 wherein a plurality of reactors are used in parallel.

11. The process according to claim 1 wherein unreacted gas exiting the outlet of the, or each, reactor is treated to remove heat.

12. The process according to claim 11 wherein the removed unreacted gas is reused.

13. The process according to claim 1 wherein two or more reactors are located in series.

14. The process according to claim 13 wherein the reactors located in series are in fluid communication with facilities located between each reactor to remove heat.

15. The process according to claim 13 or 14 wherein hydrogen and carbon monoxide containing stream exiting the last stage of the series of interconnected reactors is recycled to any suitable point in the process.

16. The process according to claim 15 wherein hydrogen and carbon monoxide containing stream exiting the last stage of the series of interconnected reactors is recycled to the first reactor.

17. The process according to claim 9 wherein groups of parallel reactors are in series communication with facilities located between each group to remove heat.

18. The process according to claim 13 wherein the heat is reused and/or rejected to cooling.

19. The process according to claim 17, wherein liquid product is removed between each group of parallel reactors with hydrogen and carbon monoxide containing stream being passed to a subsequent reaction group in the series.

20. The process according to claim 19 wherein hydrogen and carbon monoxide containing stream exiting the last stage of a series of interconnected reactors is recycled to any suitable point in the process.

21. The process according to claim 20 wherein the stream is recycled to the inlet of the first reactor.

22. The process according to claim 9 wherein a hydrogen rich stream is fed to the second and/or one or more of any subsequent reactors.

23. The process according to claim 1 wherein the reaction temperature is from about 190° C. to about 250° C.

24. The process according to claim 1 wherein the reaction pressure is from about 20 bara to about 80 bara.

* * * * *